United States Patent [19]

Huebner

[11] 4,147,786
[45] Apr. 3, 1979

[54] 1-INDOLYLALKYL-3-OR 4-TRIMETHYLENEURIDO-PIPERIDINES

[75] Inventor: Charles F. Huebner, Chatham, N.J.

[73] Assignee: Ciba-Geigy Corporation, Ardsley, N.Y.

[21] Appl. No.: 797,151

[22] Filed: May 16, 1977

Related U.S. Application Data

[60] Division of Ser. No. 654,254, Feb. 2, 1976, Pat. No. 4,073,911, which is a continuation-in-part of Ser. No. 556,600, Mar. 10, 1975.

[51] Int. Cl.$^2$ .................. A61K 31/505; C07D 401/14
[52] U.S. Cl. ..................... 424/251; 544/316; 544/330; 544/331; 544/332; 546/201
[58] Field of Search ............... 260/256.4 C, 256.4 N, 260/256.5 R; 424/251; 544/316, 332, 330, 331

[56] References Cited

U.S. PATENT DOCUMENTS 3,527,761  9/1970  Archibald et al. .............. 260/293
3,655,674  4/1972  Archibald ..................... 260/293.61

FOREIGN PATENT DOCUMENTS 1,425,354  2/1976  United Kingdom.

Primary Examiner—Donald G. Daus
Assistant Examiner—James H. Turnipseed
Attorney, Agent, or Firm—Theodore O. Groeger

[57] ABSTRACT 1-(Indolyl-3-alkyl)-3- or 4-(ureido or guanidino)-piperidines, e.g. those of the formula

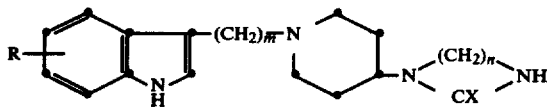

R=H; alkyl; free, etherified or esterified OH or SH; $CF_3$, $NO_2$ or $NH_2$
m=1-4;
n=2 or 3;
X=O, S or NH acyl derivatives and salts thereof are antihypertensive agents.

8 Claims, No Drawings

1-INDOLYLALKYL-3-OR 4-TRIMETHYLENEURIDO-PIPERIDINES

CROSS-REFERENCE TO RELATED APPLICATION

This is a division of copending application Ser. No. 654,254, filed Feb. 2, 1976 (now U.S. Pat. No. 4,073,911), which, in turn, is a continuation-in-part of application Ser. No. 556,600, filed Mar. 10, 1975.

SUMMARY OF THE DISCLOSURE

The present invention concerns and has for its object the provision of new 1-(indolyl-3-alkyl)-3 or 4-(ureido or guanidino)-piperidines, more particularly of those corresponding to Formula I

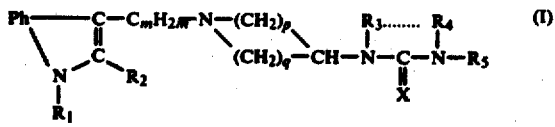

wherein Ph is unsubstituted 1,2-phenylene or 1,2-phenylene substituted by one or two identical or different members selected from lower alkyl; free, etherified or esterified hydroxy or mercapto, such as lower alkoxy, lower alkylenedioxy, benzyloxy, lower alkylmercapto or halogeno; trifluoromethyl; nitro; or amino; each of $R_1$ and $R_2$ is hydrogen or lower alkyl; each of $R_3$ and $R_4$ is hydrogen, lower alkyl or $(R_3+R_4)$ is Ph or lower alkylene separating both nitrogens by 2 to 4 carbon atoms; $R_5$ is hydrogen, lower alkyl or HPh; X is oxygen, sulfur, imino or lower alkylimino; m is an integer from 1 to 7; each of p and q is an integer from 1 to 3, but $(p+q)=4$; or of therapeutically acceptable acid addition salts thereof; of corresponding pharmaceutical compositions and of methods for the preparation and application of these products, which are useful hypotensive and antihypertensive agents.

DESCRIPTION OF THE PREFERRED EMBODIMENTS

The 1,2-phenylene group Ph is preferably monosubstituted, and its substituents illustrated by the following groups: lower alkyl, e.g. methyl, ethyl, n- or i-propyl or -butyl; hydroxy; mercapto; lower alkoxy, e.g. methoxy, ethoxy, n- or i-propoxy or -butoxy, lower alkylenedioxy, e.g. methylenedioxy, 1,1- or 1,2-ethylenedioxy; benzyloxy; lower alkylmercapto, e.g. methyl- or ethylmercapto; halogeno, e.g. fluoro, chloro or bromo; trifluoromethyl; nitro or amino. Each of $R_1$ to $R_5$ is preferably hydrogen, but also lower alkyl, advantageously methyl, or another of those mentioned above; $R_5$ may also be phenyl or substituted phenyl, as illustrated by H—Ph above; and $(R_3+R_4)$ may also be 1,2-phenylene or such substituted group illustrated above for Ph; but $(R_3+R_4)$ preferably represent lower alkylene separating both nitrogens by preferably 2 or 3 carbon atoms, e.g. 1,2-ethylene, 1,2- or 1,3-propylene, 1,2-, 1,3- or 2,3-butylene. X is preferably oxygen, but also sulfur, imino or lower alkylimino, e.g. methyl- or ethylimino. Of said integers m is preferably 1 to 4 and $C_mH_{2m}$ advantageously represents methylene, 1,1- or 1,2-ethylene, 1,2- or 1,3-propylene 1,2-, 1,3- or 1,4-butylene; and each p and q is preferably two.

In the compounds of Formula I, wherein at least one of $R_3$ to $R_5$ is hydrogen and X is O or S, said group can also be etherified by lower alkyl, preferably methyl or ethyl (thus forming tautomeric isoureidopiperidines); and said compounds having hydrogen attached to nitrogen or phenolic oxygen or sulfur, can also be acylated by lower alkanoyl or aralkanoyl, e.g. acetyl, propionyl, pivaloyl, benzoyl or phenacetyl; and all basic compounds obtained can be in the form of therapeutically useful acid addition salts, e.g. derived from the acids listed below. As used above and hereinafter in connection with organic radicals or compounds respectively, the term "lower" defines such with up to 7, preferably up to 4, and advantageously 1 or 2 carbon atoms.

The compounds of the invention exhibit valuable pharmacological properties, for example, hypotensive and antihypertensive effects. This can be demonstrated in animal tests, using advantageously mammals, such as rats, dogs or monkeys, as test object. The compounds of the invention can be applied to the animals enterally, e.g. orally, or parenterally, e.g. subcutaneously, intraperitoneally or intravenously, for example in the form of aqueous solutions or starchy suspensions. The dosage may range between about 0.1 to 100 mg/kg/day, preferably between about 1 and 75 mg/kg/day, especially between about 10 and 50 mg/kg/day. Said effects are observed in either normotensive animals, e.g. dogs or monkeys, or hypertensive animals, e.g. spontaneous hypertensive rats or renal hypertensive dogs. Their blood pressure is either indirectly recorded by sphygmomanometry, or directly via a catheter placed, for example, in the dog's femoral artery, which is connected to a transducer and recorder. Also an increase of the blood flow, for example in the dog's perfused hind limb preparation, can be observed.

Thus, for example, the 1-[2-(5-chloro or methoxy-indolyl-3)-ethyl]-4-(1,3-ethyleneureido)-piperidines or their hydrochlorides, four illustrative members of the compounds of Formula I, when orally applied within gelatin capsules at a dose of about 20 to 40 mg/kg/day to unanesthetized normotensive squirrel monkeys, or intravenously applied in saline solution at a dose of about 1 to 10 mg/kg/day to anesthetized normotensive dogs, or when orally applied within a starch suspension and a stomach tube to spontaneous hypertensive rats at a dose of about 30 to 100 mg/kg/day, decrease consistently the blood pressure, and often the heart rate also, through long periods of time.

Accordingly, the compounds of the invention are valuable hypotensive, antihypertensive and vasodilating agents. Moreover, they are also valuable intermediates in the preparation of other useful products, especially of pharmacologically active compounds.

Particularly useful are compounds of Formula I, wherein Ph is 1,2-phenylene unsubstituted or monosubstituted by lower alkyl, hydroxy, mercapto, lower alkoxy, lower alkylenedioxy, benzyloxy, lower alkylmercapto, halogeno, trifluoromethyl, nitro or amino; each of $R_1$ and $R_2$ is hydrogen or lower alkyl; each of $R_3$ and $R_4$ is hydrogen, lower alkyl or $(R_3+R_4)$ is Ph or lower alkylene separating both nitrogens by 2 or 3 carbon atoms; $R_5$ is hydrogen, lower alkyl or HPh; X is oxygen, sulfur, imino or lower alkylimino; m is an integer from 1 to 4; each of p and q is an integer from 1 to 3, but $(p+q)=4$; or a lower alkanoyl derivative of the compounds having hydrogen attached to nitrogen, oxygen or sulfur; or therapeutically acceptable acid addition salts thereof.

Preferred compounds of the invention are those of Formula I, wherein Ph is 1,2-phenylene unsubstituted or substituted by hydroxy, mercapto, alkyl, alkoxy or alkylmercapto with up to 4 carbon atoms, benzyloxy, halogeno, trifluoromethyl, nitro or amino; each of $R_1$, $R_2$ and $R_5$ is hydrogen or alkyl with up to 4 carbon atoms; each of $R_3$ and $R_4$ is hydrogen or alkylene with 2 to 4 carbon atoms separating both nitrogens by 2 or 3 carbon atoms; X is oxygen nitrogen or imino; m is an integer from 1 to 4 and each of p and q is the integer 2; or therapeutically acceptable acid addition salts thereof.

Outstanding on account of their usefulness are compounds of Formula II

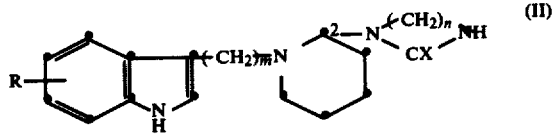

wherein R is hydrogen, hydroxy, mercapto, alkyl, alkoxy or alkylmercapto with up to 4 carbon atoms, benzyloxy, halogeno, trifluoromethyl, nitro or amino; m is an integer from 1 to 4; n is the integer 2 or 3 and X is oxygen, sulfur or imino; or therapeutically acceptable acid addition salts thereof.

More preferred compounds are those of Formula II, wherein R is hydrogen, methyl, hydroxy, mercapto, methoxy, benzyloxy, methylmercapto, fluoro, chloro, bromo, trifluoromethyl, nitro or amino, preferably in the 5 or 6 positions; m is an integer from 1 to 4; n is the integer 2 or 3 and X is oxygen, sulfur or imino; or therapeutically acceptable acid addition salts thereof.

The most preferred compounds of this invention are those of Formula II, wherein R is methoxy or chloro in the 5 or 6-positions, m=n=2 and X=O, or therapeutically acceptable acid addition salts thereof.

The compounds of this invention are prepared according to conventional methods, for example by:

(a) condensing reactive esters of indolyl-3-alkanols III with 3 or 4-(ureido or guandino)-piperidines IV:

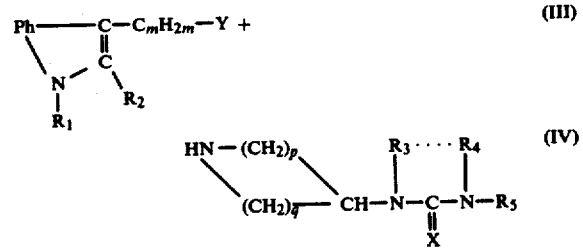

wherein Y is a reactively esterified hydroxy group, for example, such esterified by a strong inorganic or organic acid, above all a hydrohalic acid, e.g. hydrochloric, hydrobromic or hydriodic acid; sulfuric or an aromatic sulfonic acid, e.g. p-toluene or p-bromobenzene sulfonic acid. Said condensation is preferably carried out in the presence of a basic condensation agent, such as an alkali or alkaline earth metal hydroxide, carbonate or bicarbonate, e.g. sodium, potassium or calcium hydroxide or carbonate, alkali metal hydrides, lower alkoxides or alkanoates, e.g. sodium hydride, methylate or acetate, as well as organic tertiary nitrogen bases, such as tri-lower alkylamines or pyridines, e.g. triethylamine or lutidine.

Another process for preparing the compounds of the invention consists in:

(b) reacting 1-(indolyl-3-alkyl)-3 or 4-aminopiperidines V with the carbonic acid derivative VI:

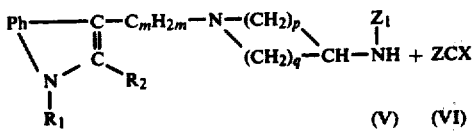

wherein $Z_1$ is $R_3$ or $R_3 \ldots R_4$—NH—$R_5$ and ZCX is an ammonium or metal cyanate or thiocyanate, a lower alkyl isourea or thiourea, a cyanogen halide or amide, carbon disulfide or oxysulfide, a carbonic acid halide or 1,1-carbonyldiimidazole, provided that at least one of Z and $Z_1$ contains nitrogen. Said reaction provides either the addition of a carbamoyl group to V if $Z_1 = R_3$, or the insertion of CX into V if $Z_1 = R_3 \ldots R_4$—NH—$R_5$. Said cyanate is preferably an alkali metal cyanate, a cyanogen halide advantageously the bromide and the carbonic acid halide preferably phosgene. Said reaction is carried out in the usual manner depending on Z. In case it is metallic, the reaction is preformed in a neutral or acidic solvent or diluent, such as a water-miscible polar solvent, for example an aqueous lower alkanol, alkanone or saturated cyclic ether, e.g. ethanol, acetone, tetrahydrofuran or dioxan, or an alkylated formamide or sulfoxide, e.g. dimethylformamide or -sulfoxide. If Z is non-metallic, a basic agent may be used as acid binder, such as an alkali or alkaline earth metal hydroxide, carbonate or bicarbonate, e.g. sodium, potassium or calcium hydroxide or carbonate, alkali metal hydrides, lower alkoxides or alkanoates, e.g. sodium hydride, methylate or acetate, as well as organic tertiary nitrogen bases, such as tri-lower alkylamines or pyridines, e.g. triethylamine or lutidine.

The compounds of the invention are also obtained by:

(c) reducing 1-(indolyl-3-terminally oxygenated alkyl)-3 or 4-(ureido or guanidino)-piperidines VII:

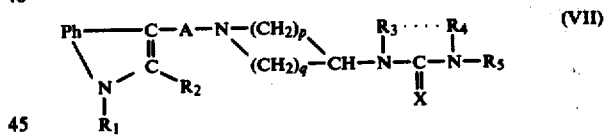

wherein A is $C_{m-1}H_{2m-2}$—CO ($m \geq 1$) or CO—$C_{m-2}H_{2m-4}$—CO ($m \geq 2$). The reduction is carried out in the usual manner, preferably with the use of simple or complex light metal hydrides, such as diborane or alane, alkali metal boro- or aluminumhydrides or -alkoxyhydrides, e.g. lithium aluminumhydride and/or sodium trimethoxyborohydride. Depending on the presence of ketonic and/or amidic carbonyl in VII, the corresponding alcohols may be formed as intermediates or byproducts, which are further reduced with the use of catalytically activated or nascent hydrogen, such as hydrogen in the presence of cobalt, palladium, platinum or rhodium catalysts, e.g. cobalt sulfide or tris-(triphenylphosphine)-rhodium chloride (which are not poisoned by sulfur), or hydrogen generated electrolytically.

Another process for preparing the compounds of the invention consists in:

(d) hydrogenating 1-(indolyl-3-alkyl or alkenyl)-3 or 4-(ureido or guanidino)-piperidines or -tetrahydropyridines VIII:

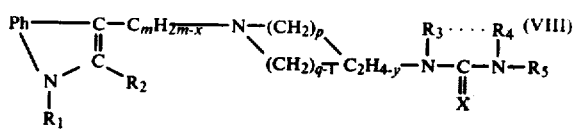

wherein each of x and y is the integer 0 or 2 and their sum x+y is 2 or 4. The hydrogenation of said olefines VIII is performed in the usual manner, preferably with the use of catalytically activated or nascent hydrogen, such as hydrogen in the presence of cobalt, palladium, platinum or rhodium catalysts, e.g. cobalt sulfide or tris-(triphenylphosphine)-rhodium chloride (which are not poisoned by sulfur), or hydrogen generated electrolytically.

The compounds of the invention are also obtained by:

(e) reductively desulfurizing 1-(2,3-dihydro-3-mercapto-2-oxindolyl-3-alkyl)-3 or 4-(ureido or guanidino)-piperidines IX:

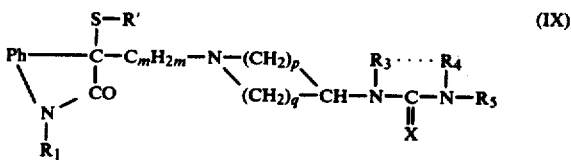

wherein R' is lower alkyl or benzyl. Said desulfurizing reduction is carried out according to methods known per se, either in one step with the use of simple or complex light metal hydrides, such as diborane or alane, alkali metal boro- or aluminumhydrides or -alkoxyhydrides, e.g. lithium aluminumhydride and/or sodium trimethoxyborohydride, advantageously alane and/or lithium aluminum hydride; or in two steps, first desulfurizing by catalytic hydrogenation, for example over Raney nickel, followed by reduction with a complex light metal hydride, e.g. lithium aluminumhydride.

Another process for preparing the compounds of the invention consists in:

(f) reductively ring-closing 1-tert. amino-2-nitrogenated phenyl-ω-(3 or 4 ureido or guanidino)-piperidinoalkenes X:

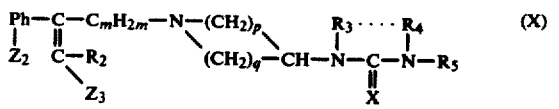

wherein $Z_2$ is a nitro, phenylazo or azido group and $Z_3$ is a tertiary amino group, such as a lower dialkylamino, alkyleneimino, morpholino or thiamorpholino group. Said ring-closure is performed in the usual manner and it occurs spontaneously as soon as $Z_2$ is converted into amino, advantageously by hydrogenation, preferably with the use of catalytically activated or nascent hydrogen, such as hydrogen in the presence of cobalt, palladium platinum or rhodium catalysts, e.g. cobalt sulfide or tris-(triphenylphosphine)-rhodium chloride (which are not poisoned by sulfur), or hydrogen generated electrolytically.

The compounds of the invention so obtained can be converted into each other according to known methods. Thus, for example, compounds with $R_1$ and $R_3$ to $R_5$ being hydrogen, and/or Ph being hydroxy-, mercapto- or amino-1,2-phenylene, or alkali metal, e.g. sodium salts thereof, can be reacted with reactive esters of lower alkanols, alkanediols or benzylalcohol respectively, e.g. such esterified by a strong inorganic or organic acid, above all a hydrohalic acid, e.g. hydrochloric, hydrobromic or hydriodic acid; sulfuric or an aromatic sulfonic acid, e.g. p-toluene or p-bromobenzene sulfonic acid, in order to obtain the corresponding N-, O- or S-substituted compounds. Depending on the molar amount of alkylating agent employed, the successive introduction of $R_1$, $R_3$, $R_4$ and $R_5$ is accomplished. Moreover, said phenols can be etherified with the use of diazoalkanes. Conversely, resulting alkaoxy- or benzyloxy-1,2-phenylene compounds may be hydrolyzed, e.g. with strong Lewis acids, such as hydrobromic acid or molten pyridinium chloride. Benzylethers may also be cleaved hydrogenolytically, e.g. with the use of catalytically activated or nascent hydrogen, such as hydrogen in the presence of cobalt, palladium, platinum or rhodium catalysts, e.g. cobalt sulfide or tris-(triphenylphosphine)-rhodium chloride (which are not poisoned by sulfur), or hydrogen generated electrolytically. A drastic version of this method may also be employed for dehalogenating Ph, or reducing a nitro group therein to amino. Nitration of Ph may also be carried out in the usual manner, for example, by heating a resulting compound with a mixture of fuming nitric acid and sulfuric acid or acetic anhydride, or a nitrate thereof in trifluoroacetic acid. An iodo atom in Ph may also be replaced by trifluoromethyl, for example by reacting the iodide with trifluoromethyl iodide in the presence of copper powder.

Finally, the compounds of the invention are either obtained in the free, basic form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide, basic salt or cation exchange preparation, e.g. an alkali metal hydroxide or carbonate. Said acid addition salts are preferably such of therapeutically acceptable inorganic or organic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyruvic, phenylacetic, benzoic 4-aminobenzoic, anthranilic, 4-hydroxybenzoic, salicyclic, 4-aminosalicylic, pamoic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylfulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The starting material of Formulae III to X is either known or, if new, can be prepared according to known procedures, e.g. those illustrated in the examples herein.

Compounds of Formula III can easily be obtained by reacting a 3-unsubstituted indole with a corresponding alkanedicarboxylic acid halide and reducing the resulting keto acid halide with lithium aluminum hydride to the corresponding alcohol and esterifying it with YH or a phosphorus or sulfonic acid halide in the usual manner.

Compounds of Formula IV are obtained from corresponding 1-benzylpiperidones, which are converted into their O-alkyloximes or Schiff's bases of diaminoalkanes or -benzenes, which are reduced, either with the use of catalytically activated or nascent hydrogen, such as hydrogen in the presence of cobalt, palladium, platinum or rhodium catalysts, e.g. cobalt sulfide or tris-(triphenylphosphine)-rhodium chloride (which are not poisoned by sulfur), or hydrogen generated electrolytically, or with the use of simple or complex light metal hydrides, such as diborane or alane, alkali metal boro- or aluminumhydrides or -alkoxyhydrides, e.g. lithium aluminumhydride and/or sodium trimethoxyborohydride, to the mono- or diamines. These are further reacted with the carbonic acid derivative ZCX, e.g. an ammonium or metal cyanate or thiocyanate, a lower alkyl isourea or thiourea, a cyanogen halide or amide, carbon disulfide or oxysulfide, a carbonic acid halide or 1,1-carbonyldiimidazole, provided that at least one of Z and $Z_1$ contains nitrogen. Finally the benzyl moiety is hydrogenolytically removed in the end, e.g. as mentioned above, preferably over palladium catalysts.

Compounds of Formula V are similarly obtained by reacting the 3- or 4-piperidone with a reactive ester of indolyl-3-alkanols, e.g. such esterified by a strong inorganic or organic acid, above all a hydrohalic acid, e.g. hydrochloric, hydrobromic or hydriodic acid; sulfuric or an aromatic sulfonic acid, e.g. p-toluene or p-bromobenzene sulfonic acid. The resulting products are converted into their O-alkyloximes or Schiff's bases of diaminoalkanes or -benzenes, which are reduced either with the use of catalytically activated or nascent hydrogen, such as hydrogen in the presence of cobalt, palladium, platinum or rhodium catalysts, e.g. cobalt sulfide or tris-(triphenylphosphine)-rhodium chloride (which are not poisoned by sulfur), or hydrogen generated electrolytically, or with the use of simple or complex light metal hydrides, such as diborane or alane, alkali metal boro- or aluminumhydrides or -alkoxyhydrides, e.g. lithium aluminumhydride and/or sodium trimethoxyborohydride, to the mono- or diamines. Also a corresponding nitropyridinium halide can be reduced with sodium borohydride and the resulting olefine hydrogenated as mentioned above.

Compounds of Formula VII are obtained by condensing a 3-unsubstituted indole with a corresponding alkanedicarboxylic acid halide and reacting the resulting compound with the piperidine IV, or reacting IV with an indolyl-3-alkanoic acid in the presence of 1,1-carbonyldiimidazole.

Compounds of Formula VIII are prepared by condensing those of III, or analogous olefines with the corresponding pyridines and reducing resulting pyridinium salts with sodium borohydride.

Compounds of Formula IX are obtained by N-chlorinating anilines with tert. butyl hypochlorite, followed by the reaction with a corresponding 2-alkylmercaptoalkanoic acid lactone, esterifying the resulting 3-hydroxyalkyl-3-alkylmercapto-2-oxindole with a phosphoric or aromatic sulfonic acid halide and condensing the reactive ester with the piperidine IV.

Finally, compounds of Formula X are obtained by condensing corresponding benzaldehydes with alkanedicarboxylic acids or alkyl esters thereof, decarboxylating and reducing the aldol condensate to the desired phenylalkanoic acid or ester, reducing them to the corresponding phenylalkanol with the use of simple or complex light metal hydrides, such as diborane or alane, alkali metal boro- or aluminumhydrides or -alkoxyhydrides, e.g. lithium aluminumhydride and/or sodium trimethoxyborohydride, esterifying it with a phosphoric or aromatic sulfonic acid halide and nitrating the reactive ester as mentioned for I above, condensing the o-nitrophenylalkanol ester with IV and thereupon with the corresponding N,N-disubstituted formamide dimethylacetal.

In case mixtures of geometrical or optical isomers of the compounds of Formulae I to X are obtained, these can be separated into the single isomers by methods in themselves known, e.g. by fractional distillation, crystallization and/or chromatography. Racemic products can likewise be resolved into the optical antipodes, for example, by separation of diastereomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g. those of Formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweetners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods respectively and contain about 0.1 to 75%, preferably about 1 to 50%, of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mg Hg.

EXAMPLE 1

The solution of 3.36 g of 3-(2-bromoethyl)-indole, 2.85 g of 4-ureidopiperidine and 3 ml of triethylamine in 25 ml dry dimethylformamide is stirred at room temperature for two days and evaporated. The residue is taken up in water, the mixture made strongly alkaline with aqueous sodium hydroxide and extracted with diethyl ether and hexane, the extract evaporated and the residue recrystallized from acetone, to yield the 1-(2-indolyl-3-ethyl)-4-ureidopiperidine of the formula

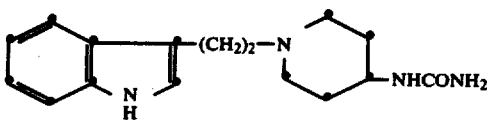

melting at 223°. It is suspended in ethanol, the suspension acidified with ethanolic hydrogen chloride, filtered and the residue recrystallized from isopropanol, to yield the corresponding hydrochloride melting at 190°.

The starting material is prepared as follows: The solution of 94.5 g of 1-benzyl-4-piperidone and 46 g of methoxyammonium chloride in 600 ml of ethanol-pyridine (1:1) is refluxed overnight and evaporated. The residue is dissolved in water, the solution made basic with 12.5% aqueous sodium hydroxide and extracted with diethyl ether. The extract is washed with water and saturated aqueous sodium hydroxide, dried and evaporated, to yield the 1-benzyl-4-methoxyiminopiperidine.

The solution of 50 g thereof in 400 ml of diethyl ether is slowly added to the suspension of 8.7 g of lithium aluminumhydride in 200 ml of diethyl ether to maintain reflux. The mixture is refluxed overnight, cooled and 8.7 ml of water, 8.7 ml of 15% of aqueous sodium hydroxide and 26 ml of water are added in this order. The mixture is filtered and the filtrate evaporated. The residue is taken up in ethanol, the solution acidified with ethanolic hydrogen chloride and diluted with diethyl ether, to yield the 4-amino-1-benzylpiperidine dihydrochloride melting at 270°-271°.

The solution of 5.62 g thereof and 2.60 g of sodium cyanate in 40 ml of water is heated on a steam bath for two hours. It is cooled in an ice bath, the resulting crystals filtered off and recrystallized from aqueous ethanol, to yield the 1-benzyl-4-ureidopiperidine melting at 140°.

The solution of 3.3 g thereof in 50 ml of acetic acid-ethanol (1:1) is hydrogenated over 660 mg of 10% palladium on charcoal at 50° and 2.7 atm. until the theoretical amount of hydrogen has been absorbed. It is filtered, the filtrate evaporated and the residue recrystallized from isopropanol, to yield the 4-ureidopiperidine melting at 160°-165°.

EXAMPLE 2

The solution of 3.5 g of 3-(2-bromoethyl)-indole, 1.5 g of 4-(1,3-propyleneureido)-piperidine, and 2.5 ml of diisopropylethylamine in 60 ml of dry dimethylformamide is stirred for two days at room temperature. The mixture is filtered, the filtrate evaporated and the residue taken up in water. The suspension is made basic with ammonium hydroxide, extracted with chloroform, the extract dried and evaporated. The residue is dissolved in hot ethanol, the solution made acidic with 4.5 N ethanolic hydrogen chloride, cooled and filtered, to yield the 1-(2-indolyl-3-ethyl)-4-(1,3-propyleneureido)-piperidine hydrochloride of the formula

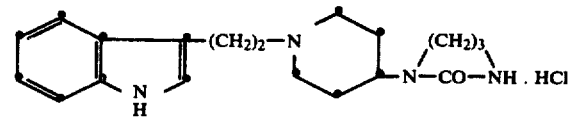

melting at 283°-285°.

The starting material is prepared as follows: To the ice cooled stirred solution of 62.5 ml of 1,3-diaminopropane in 100 ml of ethanol, 30 g of 1-benzyl-4-piperidone are added dropwise. The mixture is hydrogenated over 2 g of pre-reduced platinum oxide at 50° and 2.7 atm. for 9 hours. After theoretical hydrogen-uptake the catalyst is filtered off, the filtrate evaporated, the residue distilled and the fraction boiling at 145°-160°/0.2 mmHg collected, to yield the 4-(3-aminopropylamino)-1-benzylpiperidine.

To the stirred, ice-cooled solution of 24.1 g thereof in 100 ml of tetrahydrofuran, 18.3 g of 1,1-carbonyldiimidazole in 250 ml of tetrahydrofuran are added dropwise. After stirring at room temperature for 18 hours the mixture is evaporated, the residue suspended in water, filtered off and recrystallized from ethanol, to yield the 1-benzyl-4-(1,3-propyleneureido)-piperidine melting at 178°-180°.

The solution of 8 g thereof in 100 ml ethanol-acetic acid (1:1) is hydrogenated over 1.5 g 10% palladium on charcoal, at 50° and 2.7 atm. for 4 hours. After filtration through filter cell and removal of the solvent, the residue is taken up in water, the mixture made strongly alkaline with 50% aqueous sodium hydroxide, extracted with chloroform, the extract dried, filtered, evaporated and the residue recrystallized from ethanol, to yield the 4-(1,3-propyleneureido)-piperidine melting at 206°-210°.

EXAMPLE 3

The solution of 5.4 g of 3-(2-bromoethyl)-5-methoxyindole, 6.75 g of 4-(1,3-ethyleneureido)-piperidine and 2 ml of triethylamine in 50 ml of anhydrous dimethylformamide is stirred at room temperature for 3 days and filtered. The filter-residue is suspended in water and the insoluble desired base filtered off. More of this material is obtained from the evaporation-residue of the filtrate, which is taken up in water, the mixture basified with ammonium hydroxide and extracted with ethyl acetate. The extract is re-extracted with diluted aqueous methane sulfonic acid, the aqueous layer made sufficiently basic with cold ammonium hydroxide and extracted with methylene chloride. This extract is dried, evaporated, the residue joined with the crude base obtained above and recrystallized from isopropanol, to yield the 1-[2-(5-methoxyindolyl-3)-ethyl]-4-(1,3-ethyleneureido)-piperidine melting at 159°-161°.

The starting material is prepared as follows: To the solution of 25 g of 5-methoxyindole in 500 ml of anhydrous diethyl ether, that of 43.2 g of oxalyl chloride in 100 ml ether is added dropwise while stirring at 15° under nitrogen. After 4 hours the red-orange solid is filtered off and washed with diethyl ether, to yield the 5-methoxyindolyl-3-glyoxalic acid chloride melting at 132°–134° with decomposition.

The solution of 15.6 g thereof in 300 ml of tetrahydrofuran is added dropwise to the suspension of 10.5 g of lithium aluminum hydride in 100 ml of tetrahydrofuran. After addition is complete, the mixture is refluxed for 2 hours, cooled and decomposed by addition of 10 ml of ethyl acetate, 10 ml of water, 20 ml of 15% aqueous sodium hydroxide and 30 ml of water. It is filtered, evaporated, the residue dissolved in diethyl ether, the solution washed with water, dried and evaporated, to yield the 3-(2-hydroxyethyl)-5-methoxyindole.

To the solution of 9.6 g thereof in 350 ml of anhydrous diethyl ether, cooled to −50° C., that of 5.3 g of phosphorus tribromide in 100 ml anhydrous diethyl ether is added dropwise. After addition is complete, the mixture is stirred at said temperature for ½ hour and then allowed to warm up to room temperature. Ice is added, the ether layer washed with saturated aqueous sodium bicarbonate and water, dried and evaporated to yield the 3-(2-bromoethyl)-5-methoxyindole.

EXAMPLE 4

The solution of 5 g of 1-(2-indolyl-3-ethyl)-4-(1,3-ethyleneureido)-1,2,5,6-tetrahydropyridine in 100 ml of 50% aqueous acetic acid is hydrogenated over 0.5 g platinum oxide at 50° and 2.7 atm. After the slow absorption of one molar equivalent of hydrogen, the catalyst is filtered off and the filtrate evaporated. Water is added, the solution made basic with ammonium hydroxide, the crystalline base filtered off and recrystallized from ethanol, to yield the 1-(2-indolyl-3-ethyl)-4-(1,3-ethyleneureido)-piperidine melting at 182°–185°.

The starting material is prepared as follows: The solution of 1.4 g of 3-(2-bromoethyl)-indole and 1 g of 4-(1,3-ethyleneureido)-pyridine in 20 ml of acetonitrile is refluxed overnight. After cooling the resulting solid is collected and recrystallized from ethanol, to yield the 1-(2-indolyl-3-ethyl)-4-(1,3-ethyleneureido)-pyridinium bromide melting at 225°–230°.

To the stirring suspension of 5.2 g thereof in 100 ml of methanol, is portionwise added 3.5 g of sodium borohydride. After stirring at room temperature for one hour, the solvent is removed and the residue recrystallized from ethanol, to yield the 1-(2-indolyl-3-ethyl)-4-(1,3-ethyleneureido)-1,2,5,6-tetrahydropyridine melting at 155°–160°.

EXAMPLE 5

1 g of 1-(2-indolyl-3-acetyl)-4-(1,3-ethyleneureido)-piperidine is added portionwise to the stirred suspension of 0.5 g of lithium aluminumhydride in 100 ml of tetrahydrofuran. After 18 hours the mixture is decomposed by the addition of 0.5 ml of water, 1 ml of 15% aqueous sodium hydroxide and 1.5 ml of water, filtered and evaporated. The basic residue is acidified with ethanolic hydrogen chloride to yield the 1-(2-indolyl-3-ethyl)-4-(1,3-ethyleneureido)-piperidine hydrochloride melting at 280°–285°.

Analogously the 1-[2-(5-bromoindolyl-3)-ethyl]-4-(1,3-ethyleneureido)-piperidine hydrochloride, m.p. 165°–170° dec. is prepared.

The starting material is prepared as follows: The mixture of 12 g of 3-indoleacetic acid, 13.5 g of 1,1-carbonyldiimidizole and 300 ml of tetrahydrofuran is stirred for one hour, whereupon the solution of 11.5 g of 4-(1,3-ethyleneureido)-piperidine in 100 ml of methylene chloride is added dropwise allowing the temperature to rise up to 50° C. After 18 hours the mixture is evaporated, the residue taken up in water and filtered. The residue is washed with diluted aqueous sodium hydroxide and recrystallized from ethanol, to yield the 1-(2-indolyl-3-acetyl)-4-(1,3-ethyleneuredio)-piperidine melting at 205°–207°.

EXAMPLE 6

To the solution of 7 g of (5-benzyloxyindole-3)-acetic acid in 100 ml of tetrahydrofuran is added with stirring 5.5 g of 1,1-carbonyldiimidazole. After one hour 4.7 g of 4-(1,3-ethyleneureido)-piperidine are added and stirring continued overnight. The highly insoluble crystalline amide separates from solution, it is filtered off, washed with water, dried in a dessicator and ground to a fine powder. This is added in portions with stirring and cooling to 25° to the solution of 2 g of lithium aluminumhydride in 50 ml of tetrahydrofuran. After stirring overnight at room temperature, the mixture is cooled in ice and treated in succession with 2 ml of water, 4 ml of 15% of aqueous sodium hydroxide and 6 ml of water. The inorganic salts are filtered off, washed with diethyl ether, the filtrate evaporated and the residue recrystallized from isopropanol to give the 1-[2-(5-benzyloxyindolyl-3)-ethyl]-4-(1,3-ethyleneureido)-piperidine melting at 149°–150°.

EXAMPLE 7

The solution of 2 g of 1-[2-(5-benzyloxyindolyl-3)-ethyl]-4-(1,3-ethyleneureido)-piperidine in 15 ml of ethanol and 15 ml of acetic acid is hydrogenated over 0.4 g of 10% palladium on carbon at room temperature and atmospheric pressure. One molar equivalent is taken up within one hour, the catalyst is filtered off and the filtrate evaporated while avoiding excessive heating. The residue is dissolved in 15 ml of water and the solution carefully made basic with ammonium hydroxide. The desired derivative separates first as resin, but crystallizes on rubbing. It is filtered off, suspended in 50 ml of isopropanol, treated with 5 ml of 4.5 N ethanolic hydrogen chloride and the suspension refluxed on the steam bath. Water is slowly added until solution occurs and on cooling, the crystalline 1-[2-(5-hydroxyindolyl-3-)-ethyl]-4-(1,3-ethyleneureido)-piperidine hydrochloride separates, m.p. 220°.

EXAMPLE 8

To the stirred solution of 2.4 g of 1-(2-indolyl-3-ethyl)-4-(2-aminoethylamino)-piperidine in 10 ml of 50% aqueous ethanol, 0.55 ml of carbon disulfide are added dropwise and the mixture is heated to 60° while the rest of the carbon disulfide is added. Thereupon the temperature is raised to 100° for one hour, 5 ml of concentrated hydrochloric acid are added and refluxing continued for 9 hours. After cooling the mixture is filtered, the residue washed with acetone and recrystallized from isopropanol, to yield the 1-(2-indolyl-3-ethyl)-4-(1,3-ethylenethioureido)-piperidine melting at 204°.

Similarly the 1-(2-indolyl-3-ethyl)-4-(1,3-ethyleneguanidino)-piperidine hydrobromide is prepared with the use of 0.88 g of cyanogen bromide, 20 ml of tetrahydrofuran and the same amount of diamine and collecting the salt after 2 hours, m.p. 200°.

The starting material is prepared as follows: The mixture of 2.24 g of the 3-(2-bromoethyl)-indole, 3.06 g of 4-piperidone monohydrate hydrochloride, 5 g of anhydrous sodium carbonate and 20 ml of dimethylformamide is stirred at room temperature for one hour. Thereupon 50 ml of dimethylformamide are added to enable stirring and after 2 days the mixture is evaporated. The residue is dissolved in water, the basic layer extracted with ethyl acetate and the organic layer re-extracted with N hydrochloric acid. The aqueous solution is made basic with 12.5% aqueous sodium hydroxide extracted with ethyl acetate and the organic layer washed with water and saturated aqueous sodium chloride. After drying it is evaporated and the solid recrystallized from ethyl acetate, to yield the 1-(2-indolyl-3-ethyl)-4-piperidone.

The solution of 4 g thereof in 30 ml of ethanol is added to the ice-cooled solution of 4.95 g of ethylene diamine in 10 ml of ethanol. This mixture is then added to 0.5 g of platinum oxide and hydrogenated at 2.7 atm. and 50°. After the theoretical hydrogen-uptake it is filtered and the filtrate evaporated, to yield the 1-(2-indolyl-3-ethyl)-4-(2-aminoethylamino)-piperidine, which is sufficiently pure.

EXAMPLE 9

To the solution of 10 g of 4-amino-1-(2-indolyl-3-ethyl)-piperidine in 100 ml of methylene chloride, is added 4.4 g of 2-chloroethylisocyanate with cooling. After standing overnight at room temperature the solvent is removed, the residue dissolved in 100 ml of ethanol, the solution treated with 2.9 g of sodium methoxide and refluxed for six hours. The mixture is concentrated to a small volume, treated with water and extracted with methylene chloride. The extract is dryed, evaporated and the residue recrystallized twice from ethanol, to yield the 1-(2-indolyl-3-ethyl)-4-(1,3-ethyleneureido)-piperidine melting at 182°-185°.

The starting material is prepared as follows: The solution of 15 g of 1-(2-indolyl-3-ethyl)-4-piperidone in 100 ml of pyridine is treated with 1.5 g of methoxyammonium chloride and heated on a steam bath for three hours. The solvent is distilled off, the residue treated with water, ammonium hydroxide and the solid filtered off, to yield the 1-(2-indolyl-3-ethyl)-4-methoxyimino-piperidine.

It is dried in a desiccator, dissolved in 150 ml of tetrahydrofuran and the solution added to the refluxing solution of 5 g of lithium aluminumhydride in 100 ml of tetrahydrofuran. After stirring and refluxing for 4 hours the mixture is cooled in ice and 4 ml of ethyl acetate, 5 ml of water, 10 ml of 15% aqueous sodium hydroxide and 15 ml of water are added in succession with stirring. The inorganic salts are filtered off, washed with diethyl ether and the filtrate evaporated, to yield the 4-amino-1-(2-indolyl-3-ethyl)-piperidine.

EXAMPLE 10

The mixture of 12 g of 1-dimethylamino-2-(2-nitro-5-chlorophenyl)-4-[4-(1,3-ethyleneureido)-piperidino]-butene, 1 g of Raney nickel and 100 ml of benzene is hydrogenated at room temperature and 2.7 atm. until the hydrogen absorption stops (approximately 3 molar equivalents are absorbed). It is filtered, the benzene solution dried and evaporated. The residue is dissolved in 50 ml of 1N aqueous methanesulfonic acid and the solution allowed to stand at room temperature for two days. (This serves to hydrolize the small amount of O-methyl ether formed in the reaction with the formamide acetal.) The aqueous solution is made alkaline with ammonium hydroxide, extracted with methylene chloride, the extract dryed and evaporated. The residue is dissolved in 25 ml of hot isopropanol, cooled, filtered and the residue recrystallized from ethanol, to yield the 1-[2-(5-chloroindolyl-3)-ethyl]-4-(1,3-ethyleneureido)-piperidine melting at 140°-142°.

The starting material is prepared as follows: The mixture of 50 g of 3-chlorobenzaldehyde, 41 g of malonic acid and 36 ml of pyridine is heated on the steam bath for 3 hours. The residue is dissolved in 200 ml of water, the solution acidified with hydrochloric acid, filtered, and the residue recrystallized from aqueous ethanol, to yield the 3-chlorocinnamic acid melting at 150°-152°.

The solution of 20 g thereof in 200 ml of acetic acid is hydrogenated over 1 g of 10% rhodium on carbon at room temperature and 2.7 atm. until one molar equivalent hydrogen has been absorbed. The catalyst is filtered off, the filtrate evaporated and the residue recrystallized from aqueous ethanol, to yield the β-(3-chlorophenyl)-propionic acid.

The solution of 35 g thereof in 100 ml of tetrahydrofuran is added to that of 8 g lithium aluminum hydride in 50 ml of diethyl ether and the mixture refluxed after 4 hours. It is cooled in ice, treated with 10 ml of ethyl acetate, 8 ml of water, 16 ml of 15% aqueous sodium hydroxide and 24 ml of water. The salts are filtered off, washed with diethyl ether, and the filtrate is evaporated, to yield the 3-(3-chlorophenyl)-propanol.

To the solution of 20 g thereof in 120 ml of pyridine, cooled in an ice bath, is added slowly with stirring 29 g of p-toluenesulfonyl chloride. The mixture is allowed to warm up to room temperature and after standing overnight, it is poured onto 200 g of ice and extracted with diethyl ether. The extract is washed with cold 4N hydrochloric acid and water, dried and evaporated to yield the corresponding tosylate.

The mixture of 10 g thereof, 5.2 g of 4-(1,3-ethyleneureido)-piperidine, 25 g of anhydrous sodium carbonate and 200 ml of 4-methyl-2-pentanone is stirred and refluxed for three days and filtered hot. The filtrate is evaporated, the residue taken up in ethyl acetate and the solution extracted with dilute aqueous methane sulfonic acid. The extract is made alkaline with ammonium hydroxide, re-extracted with methylene chloride, the extract dried and evaporated, to yield the 1-[3-(3-chlorophenyl)-propyl]-4-(1,3-ethyleneureido)-piperidine.

To the solution of 4.9 g thereof in 15 ml of acetic acid is added with cooling the mixture of 0.4 ml of fuming nitric acid and 1.2 ml of acetic anhydride while stirring at room temperature. After standing overnight, the mixture is poured into water, extracted with ethyl acetate, the extract washed with cold ammonium hydroxide, dried and evaporated, to yield the 1-[3-(2-nitro-5-chlorophenyl)-propyl]-4-(1,3-ethyleneureido)-piperidine.

The mixture of 10 g thereof and 9.3 g of dimethylformamide dimethylacetal is heated to 165° and the methanol formed distilled off by use of a Vigreux column. After three hours the excess reagent is removed by heating to 120° in vacuo, to yield the 1-dimethylamino-2-(2-nitro-5-chlorophenyl)-4-[4-(1,3-ethyleneureido)-piperidino]-butene of the formula

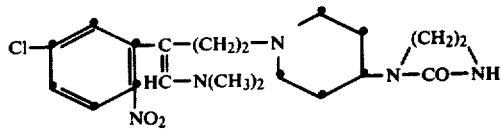

EXAMPLE 11

To the cooled, stirred solution of 10 g of 1-(2-indolyl-3-ethyl)-4-ureidopiperidine in 200 ml of dry dimethylformamide is added 5 g of a 50% mineral oil dispersion of sodium hydride. After the hydrogen evolution has ceased, the solution of 3.1 ml of 1,2-dibromoethane in 25 ml of dimethylformamide is added with stirring and cooling with tap water. After 24 hours the mixture is heated to 50° for 12 hours, cooled and 5 ml of acetic acid are added. The precipitate is collected, suspended in 20% aqueous sodium hydroxide and the mixture extracted with methylene chloride. The extract is evaporated the the residue recrystallized from ethanol several times, to yield the 1-(2-indolyl-3-ethyl)-4-(1,3-ethyleneureido)-piperidine melting at 182°-185°.

EXAMPLE 12

To a stirred suspension prepared from 0.46 g of sodium and 200 ml of liquid ammonia is first added 3.1 g of 1-(2-indolyl-3-ethyl)-4-(1,3-ethyleneureido)-piperidine and then dropwise the solution of 1.49 g of methyl iodide in 30 ml of anhydrous diethyl ether. It is evaporated, water is added and the mixture extracted with chloroform. The extract is dried and evaporated. The residue is chromatographed on a thin layer of silica gel with ethylacetate-methanol-ammonium hydroxide (90:5:5) as the developing solution. The fraction with Rf=5.0 is the 1-[2-(1-methylindolyl-3)-ethyl]-4-(1,3-ethyleneureido)-piperidine melting at 184°-187°, and that with Rf=6.0 is the 1-(2-indolyl-3-ethyl)-4-(3-methyl-1,3-ethyleneureido)-piperidine.

EXAMPLE 13

To a stirred solution of 2 g of 1-(2-indolyl-3-ethyl)-4-(1,3-ethyleneureido)-piperidine in 100 ml of acetic acid is added over four hours, 4.8 g of sodium borohydride in pellet form. The last 10% is added over one half hour while heating the reaction mixture to 50°. When all the borohydride has dissolved, the mixture is concentrated to a small volume, the concentrate diluted with 100 ml water and extracted with methylene chloride. The extract is dryed, evaporated and the residue recrystallized from ethyl acetate, to yield the 1-(2-indolyl-3-ethyl)-4-(3-ethyl-1,3-ethyleneureido)-piperidine melting at 145°. Its hydrochloride is prepared by treating a suspension thereof in hot isopropanol with excess ethanolic hydrogen chloride; on cooling the salt separates, m.p. 239°-240° dec.

EXAMPLE 14

The mixture of 3.1 g of 3-(2-bromoethyl)-indole, 2.9 g of 4-(3-phenylureido)-piperidine, 3.2 ml of triethylamine and 30 ml of dimethylformamide is stirred at room temperature for 3 days. It is diluted with 200 ml of water, cooled, filtered and the residue recrystallized from ethanol, to yield the 1-(2-indolyl-3-ethyl)-4-(3-phenylureido)-piperidine melting at 203°-206°.

The starting material is prepared as follows: To the solution of 25 g of 4-aminopyridine in 150 ml of benzene is added dropwise with stirring the solution of 31.6 g of phenylisocyanate in 50 ml of benzene at 40°. After one hour, the pure crystalline 1-phenyl-3-(4-pyridyl)-urea is filtered off, m.p. 155°-156°.

5 g thereof are hydrogenated over 5 g of 10% palladium on charcoal in 80 ml of acetic acid at 70° and 2.7 atm. After the absorption of 3 molar equivalents of hydrogen (2 days) the mixture is filtered and the filtrate evaporated. The residue is taken up in water, extracted with methylene chloride, the extract evaporated and the residue recrystallized from acetone, to yield the 4-(3-phenylureido)-piperidine melting at 172°-175°.

EXAMPLE 15

According to the methods illustrated in the previous examples, advantageously Examples 1-3, the compounds of the following formula are prepared from equivalent amounts of the corresponding starting materials: bz=benzyl

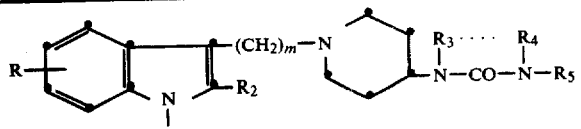

| No. | R | $R_1$ | $R_2$ | $R_3 + R_4$ | $R_5$ | m | Salt | m.p. °C. |
|---|---|---|---|---|---|---|---|---|
| 1 | H | H | H | H H | $C_6H_5$ | 2 | — | 203-206 |
| 2 | H | H | H | $CH_2-CH_2$ | H | 2 | — | 182-185 |
| 3 | H | $CH_3$ | H | " | H | 2 | — | 184-187 |
| 4 | H | H | $CH_3$ | " | H | 2 | HCl | 170 dec. |
| 5 | 7-$CH_3$ | H | H | " | H | 2 | " | 275 dec. |
| 6 | 6-i-$C_3H_7$ | H | H | " | H | 2 | — | 224-226 |
| 7 | 5-OH | H | H | " | H | 2 | " | 220 dec. |
| 8 | 7-$OCH_3$ | H | H | " | H | 2 | — | 220-225 |
| 9 | 5-Obz | H | H | " | H | 2 | — | 149-150 |
| 10 | 5-F | H | H | " | H | 2 | HCl | 290 dec. |
| 11 | 5-Cl | H | H | " | H | 2 | " | 278 dec. |
| 12 | 6-Cl | H | H | " | H | 2 | " | 301 dec. |
| 13 | 7-Cl | H | H | " | H | 2 | — | 207-212 |
| 14 | 5-Br | H | H | " | H | 2 | HCl | 170 dec. |
| 15 | H | H | H | " | H | 3 | " | 273-275 |
| 16 | H | H | H | " | $C_6H_5$ | 2 | HBr | 233-236 |
| 17 | H | H | H | o-$C_6H_4$ | H | 2 | — | 242-244 |

Several of the starting materials used are prepared as follows: To the stirred suspension prepared from 0.85 g of sodium in 200 ml of liquid ammonia is first added 3.0 g of tryptophol, then dropwise 3.3 g of methyl iodide in 100 ml of diethyl ether. The ammonia is allowed to evaporate, water is added to the residue and the mixture extracted with chloroform. The extract is dried and evaporated, to yield the 1-methyl-tryptophol.

To the stirred, cooled solution of 1.6 g thereof in 35 ml of anhydrous diethyl ether is added the solution of 0.31 ml of phosphorous tribromide in 10 ml of diethyl ether. After stirring overnight, the mixture is decomposed with ice, washed with water aqueous sodium bicarbonate and saturated aqueous sodium chloride, dried and evaporated to yield the 3-(2-bromoethyl)-1-methylindole.

To the stirred solution of 5.6 g p-chloroaniline in 150 ml of methylene chloride is added dropwise 4.7 ml of t-butyl hypochlorite in 20 ml of methylene chloride at −65°. After ten minutes, the solution of 5.75 g of 2-ethylmercaptobutyrolactone in 20 ml of methylene chloride is added dropwise and the temperature held at −65° for two hours. Then the solution of 6.1 ml of triethylamine in 20 ml of methylene chloride is added dropwise and the mixture is allowed to warm up to room temperature. 50 ml of water are added with stirring and the precipitate filtered off, to yield the 5-chloro-3-(2-hydroxyethyl)-3-ethylmercapto-2-oxindole melting at 132°–135°.

The solution of 3 g thereof in 30 ml of tetrahydrofuran is added to 35 ml of a 1.2 molar solution of aluminum hydride in tetrahydrofuran. After refluxing for 24 hours the mixture is cooled and 25 ml of 20% phosphoric acid containing 0.5 g of urea are added. The organic layer is separated, dried and evaporated, to yield the 5-chlorotryptophol.

Analogously, or according to Example 3, the 7-methoxy-tryptophol, b.p. 145°–158°/0.1 mmHg and the 6-isopropyltryptophol, b.p. 165°/0.1 mmHg are prepared.

To the solution of 12.6 g of N-phenylethylenediamine in 200 ml of methanol, 50 ml of 4.1 N ethanolic hydrogen chloride are added dropwise followed by 18.9 g of 1-benzyl-4-piperidone in 100 ml of methanol. Then, 9.45 g sodium cyanoborohydride are added in portions while stirring at room temperature. After 72 hours the mixture is filtered, the residue dissolved in water and the solution made basic with 12.5% aqueous sodium hydroxide. It is extracted with methylene chloride, dried and evaporated to yield the 1-benzyl-4-(2-phenylaminoethylamino)-piperidine.

To the stirring solution of 14 g thereof in 100 ml of dry benzene, 170 ml of 12.5% phosgene in benzene are added dropwise at room temperature. After stirring overnight the gelatinous precipitate is filtered through a sintered glass funnel, the solid dissolved in hot water, the solution made basic with ammonium hydroxide and the precipitate filtered off, to yield the 1-benzyl-4-(3-phenyl-1,3-ethyleneureido)-piperidine melting at 168°–170°.

The solution of 10 g thereof in 200 ml ethanol acetic acid (1:1) is hydrogenated over 1 g of 10% palladium on charcoal for 8 hours at 50° and 2.7 atm. After filtration through filter cell and removal of the solvent, the residue is made basic with 25% aqueous sodium hydroxide and the mixture extracted with diethyl ether. The organic layer is dried and evaporated to yield the 4-(3-phenyl-1,3-ethyleneureido)-piperidine.

EXAMPLE 16

The solution of 3 g of 1-[2-(5-chloro-3-ethylmercapto-2-oxindolinyl-3)-ethyl]-4-(1,3-ethyleneureido)-piperidine in 50 ml of tetrahydrofuran is added to 25 ml of 1.2 molar aluminum hydride in benzene and the mixture is stirred and refluxed for 24 hours. After cooling 11 ml of tetrahydrofuran-water (1:1) are added, followed by the solution of 2.3 g of sodium hydroxide in 60 ml of water. The organic phase is separated, dried, evaporated and the residue taken-up in hot isopropanol. The solution is treated with ethanolic hydrogen chloride until acidic, cooled and filtered, to yield the 1-[2-(5-chloroindolyl-3)-ethyl]-4-(1,3-ethyleneureido)-piperidine hydrochloride melting at 276°–278° with decomposition.

The starting material is prepared as follows: To the cooled, stirred solution of 21 g of 5-chloro-3-(2-hydroxyethyl)-3-ethylmercapto-2-oxindole in 150 ml of pyridine is added in portions 25 g of p-toluenesulfonyl chloride. After standing overnight at room temperature, the mixture is poured into ice water and made acidic with hydrochloric acid, filtered and the residue washed with diethyl ether, to yield the corresponding tosylate melting at 100°.

The mixture of 2 g thereof, 0.8 g of 4-(1,3-ethyleneureido)-piperidine, a crystal of sodium iodide and 10 g of anhydrous sodium carbonate in 100 ml of 4-methyl-2-pentanone is stirred and refluxed for 3 days. The inorganic salts are filtered off, the filtrate evaporated and the residue recrystallized from ethanol to yield the 1-[2-(5-chloro-3-ethylmercapto-2-oxindolinyl-3)-ethyl]-4-(1,3-ethyleneureido)-piperidine, melting at 135°.

EXAMPLE 17

Preparation of 10,000 tablets each containing 25 mg of the active ingredient:

Formula

| | |
|---|---|
| 1-[2-(5-chloroindolyl-3)-ethyl]-4-(1,3-ethyleneureido)-piperidine | 250.00 g |
| Lactose | 1,956.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

EXAMPLE 18

To the stirred mixture of 22 g of lithium aluminumhydride and 2.5 lt of tetrahydrofuran, 72 g of finely powdered 1-[2-(6-chloroindolyl-3)-acetyl]-4-(1,3- ethyleneureido)-piperidine are added during about 20 minutes at −5° to 0°. After completed addition the mixture is stirred ½ hour in an ice bath and 18 hours at room temperature. It is again cooled to 0°, and combined with 20 ml of ethyl acetate, 22 ml of water, 44 ml of 15% aqueous sodium hydroxide and 66 ml of water. After 3 hours it is filtered, the residue washed with 300 ml of hot tetrahydrofuran, the filtrate evaporated and the residue triturated with 200 ml of diethyl ether, to yield 59 g of 1-[2-(6-chloroindolyl-3)-ethyl]-4-(1,3-ethyleneureido)-piperidine melting at 208°-210°. Another 9 g thereof can be extracted from the finely ground lithium aluminum salts with chloroform.

183 g thereof are dissolved in 2.5 lt of refluxing ethanol, the solution is filtered hot and the stirred filtrate combined with 74 ml of 7.9 N ethanolic hydrogen chloride at 70°. 200 ml of ethanol are added to aid stirring and after cooling to room temperature the mixture is filtered and the residue washed with diethyl ether, to yield the corresponding hydrochloride melting at 298°-300°, it is identical with that obtained according to Example 15, No. 12.

The starting material is prepared as follows: To the solution of 265 ml of acetic acid, 116 ml of 36% aqueous formaldehyde and 190 ml of 40% aqueous dimethylamine, 226.5 g of 6-chloroindole are added portionwise during 45 minutes while stirring at about 40°. The mixture is heated to 60° for 15 minutes and stirred at room temperature for 1 hour. It is cooled to 10°, combined with 500 ml of water, 400 ml of 25% aqueous sodium hydroxide and 100 ml of 20% aqueous sodium carbonate, stirred for ½ hour at 10°-20°, and filtered. The filtrate is combined with 250 ml 12% aqueous sodium carbonate, stirred for ½ hour, again filtered, both residues are washed with about 3 lt of water, combined and dried, to yield 300 g of 6-chloro-3-dimethylaminomethylindole melting at 130°-133°.

The solution of 294.3 g thereof in 3 lt of methanol is added to the stirred solution of 184 g of potassium cyanide in 370 ml of water, followed by the dropwise addition of 210 ml of methyl iodide at 25°-30°. The mixture is stirred at room temperature for 18 hours, filtered and the filtrate concentrated to about 20% of its volume. The concentrate is filtered and the filtrate evaporated, to yield another about 200 g batch. Each of said batches is dissolved in 1 lt of ethyl acetate, the solution washed with 1 lt of water, dried, evaporated and the residue recrystallized from isopropanol, to yield 217 g of 2-(6-chloroindolyl-3)-acetonitrile melting at 79°-83°.

216.7 g thereof are refluxed with 2.2 lt of 20% aqueous potassium hydroxide for 3 hours. The mixture is cooled to room temperature, filtered, the filtrate combined with 600 ml of water and acidified by the dropwise addition of 600 ml of concentrated hydrochloric acid while stirring at 20°. The mixture is filtered, the residue washed with water, dissolved in 3 lt of diethyl ether, the solution washed with saturated aqueous sodium chloride, dried and evaporated, to yield 207 g of 2-(6-chloroindolyl-3)-acetic acid melting at 165°-168°.

To the solution of 92.6 g thereof in 920 ml of anhydrous tetrahydrofuran, 93 g of 1.1'-carbonyldiimidazole are added during 20 minutes while stirring at room temperature under nitrogen. Stirring is continued until carbon dioxide evolution ceases, whereupon the solution of 90 g of 4-(1,3-ethyleneureido)-piperidine in 440 ml of isopropanol is added. The mixture is stirred at room temperature overnight, cooled with ice, filtered and the residue washed with ice cold tetrahydrofuran, to yield 135.5 g of 1-[2-(6-chloroindolyl-3)-acetyl]-4-(1,3-ethyleneureido)-piperidine melting at 225°-227°.

EXAMPLE 19

The solution of 2 g of 1-(1-hydroxy-2-indolyl-3-ethyl)-4-(1,3-ethyleneureido)-piperidine in 50 ml of acetic acid is hydrogenated over 1 g of 10% of saturated palladium on charcoal at 50° and 3 atm until one molar equivalent of hydrogen has been absorbed. The mixture is filtered, the filtrate concentrated, the concentrate made basic with aqueous ammonia, filtered and the residue recrystallized from ethanol, to yield the 1-(2-indolyl-3-ethyl)-4-(1,3-ethyleneureido)-piperidine melting at 182°-185°. It is identical with that obtained according to Example 4.

The starting material is prepared as follows: To the solution of 20 g of indole in 300 ml of anhydrous diethyl ether, 25 g of oxalyl chloride in 80 ml of diethyl ether are added dropwise while stirring at 0°. The mixture is stirred 20 minutes longer, filtered and the residue washed with diethyl ether, to yield the 2-(indolyl-3)-glyoxylic acid chloride melting at 134°.

The suspension of 20 g thereof in 200 ml of methylene chloride is added dropwise to the solution of 33.8 g of 4-(1,3-ethyleneureido)-piperidine in 200 ml of methylene chloride while stirring and cooling with ice. After stirring the mixture at room temperature overnight it is filtered nd the filtrate evaporated. The residue is dissolved in ethyl acetate, the solution washed with N hydrochloric acid, water and saturated aqueous sodium chloride, dried and evaporated, to yield the 1-(indolyl-3)-2-[4-(1,3-ethyleneureido)-piperidino]-glyoxal melting at 234°.

6.8 g thereof are added portionwise to the prerefluxed suspension of 1.52 g of lithium aluminumhydride in 200 ml of tetrahydrofuran while stirring at −5°. Thereupon the mixture is stirred for 18 hours at room temperature, cooled with ice and combined with 1.5 ml of water, 3 ml of 15% of aqueous sodium hydroxide and 4.5 ml of water, filtered, the filtrate evaporated and the residue recrystallized from ethanol, to yield the 1-(1-hydroxy-2-indolyl-3-ethyl)-4-(1,3-ethyleneureido)-piperidine melting at 202°-204°.

EXAMPLE 20

The mixture of 3.26 g of 5-nitro-3-(2-tosyloxyethyl)-indole, 4.55 g of 4-(1,3-ethyleneureido)-piperidine and 30 ml of dimethylformamide is stirred at room temperature for 5 days. It is filtered, the filtrate concentrated and the concentrate diluted with aqueous ammonia. The mixture is extracted with ethyl acetate, the extract dried, evaporated and the residue recrystallized from ethanol, to yield the 1-[2-(5-nitroindolyl-3)-ethyl]-4-(1,3-ethyleneureido)-piperidine melting at 148°-155°. It is suspended in hot isopropanol, the suspension acidified with 5 N ethanolic hydrogen chloride while boiling and diluting with water until dissolution occurs. On cooling the corresponding hydrochloride separates, melting at 300°-305°.

The starting material is prepared as follows: To the mixture of 200 ml of 1.1 N alane in benzene and 250 ml of tetrahydrofuran, that of 25.8 g of ethyl 2-(5-nitroindolyl-3)-acetate and 100 ml of tetrahydrofuran is added dropwise while stirring at 0°. After stirring for 3 hours at 0°-10°, 200 ml of 20% aqueous phosphoric acid, containing 2 g of urea, are added dropwise, the supernatant organic layer separated, dried and evaporated, to yield the 3-(2-hydroxyethyl)-5-nitroindole.

To the solution of 2 g thereof in 30 ml of pyridine 3.24 g of tosyl chloride are added while stirring at 5°. After 3 hours the mixture is poured onto ice, extracted with diethyl ether, the extract washed with water and N hydrochloric acid, dried and evaporated, to yield the 5-nitro-3-(2-tosyloxyethyl)-indole.

EXAMPLE 21

The mixture of 5 g of 1-[2-(5-chloro-3-ethylmercapto-2-oxindolinyl-3)-ethyl]-4-(1,3-ethyleneureido)-piperidine, 200 ml of ethanol and 50 g of Raney Nickel is refluxed for 12 hours, filtered and the filtrate evaporated, to yield the 1-[2-(5-chloro-2-oxindolinyl-3)-ethyl]-4-(1,3-ethyleneureido)-piperidine. It is dissolved in 50 ml of tetrahydrofuran and the solution added dropwise to the mixture of 2 g of lithium aluminum hydride and 200 ml of tetrahydrofuran. The mixture is stirred overnight at room temperature, combined with 2 ml of ethyl acetate, 2 ml of water, 4 ml of 15% aqueous sodium hydroxide and 6 ml of water, filtered and the filtrate evaporated. The residue is taken up in isopropanol and the solution acidified with ethanolic hydrogen chloride, to yield the 1-[2-(5-chloroindolyl-3)-ethyl]-4-(1,3-ethyleneureido)-piperidine hydrochloride, m.p. 276°–278° (dec.); it is identical with that obtained according to Example 16.

EXAMPLE 22

According to the methods illustrated in the previous Examples, advantageously Examples 1-3 or 18, the following compounds are prepared from equivalent amounts of the corresponding starting materials:

(1) 1-[2-(5-methylindolyl-3)-ethyl]-4-(1,3-ethyleneureido)-piperidine, m.p. 148°–150° (ethanol);
(2) 1-[2-(5,6-dimethylindolyl-3)-ethyl]-4-(1,3-ethyleneureido)-piperidine, m.p. 156°–158° (ethanol);
(3) 1-[2-(5,7-dimethylindolyl-3)-ethyl]-4-(1,3-ethyleneureido)-piperidine, m.p. 156°–158° (ethanol);
(4) 1-[2-(4-chloroindolyl-3)-ethyl]-4-(1,3-ethyleneureido)-piperidine, m.p. 276°–278° (dec., isopropanol).

The names of compounds No. 1 to 17 of the table in Example 15 are the following: 1,1-(2-indolyl-3-ethyl)-4-(3-phenylureido)-piperidine, 2.1-(2-indolyl-3-ethyl)-4-(1,3-ethyleneureido)-piperidine, 3-5. 1-[2-(1-, 2- or 7-methylindolyl-3)-ethyl]-4-(1,3-ethyleneureido)-piperidine, 6-14.1-[2-(6-isopropyl-, 5-hydroxy-, 7-methoxy-, 5-benzyloxy-, 5-fluoro, 4-chloro-, 6-chloro-, 7-chloro- or 5-bromoindolyl-3)-ethyl]-4-(1,3-ethyleneureido)-piperidine, 15.1-(3-indolyl-3-propyl)-4-(1,3-ethyleneureido)-piperidine, 16.1-(3-indolyl-3-propyl)-4-(3-phenyl-1,3-ethyleneureido)-piperidine and 17.1-(3-indolyl-3-propyl)-4-(1,3-o-phenyleneureido)-piperidine or the hydrochloride or hydrobromide thereof.

EXAMPLE 23

Preparation of 10,000 capsules each containing 10 mg of the active ingredient.

Formula

| | |
|---|---|
| 1-[2-(6-chloroindolyl-3)-ethyl]-4-(1,3-ethyleneureido)-piperidine | 100.0 g |
| Lactose | 1,800.0 g |
| Talcum powder | 100.0 g |

Procedure

All the powders are passed through a screen with openings of 0.6 mm. Then the drug substance is placed in a suitable mixer and mixed first with the talcum, then with the lactose until homogeneous. No. 3 gelatin capsules are filled with 200 mg each, uring a capsule filling machine.

I claim:

1. A compound of the formula

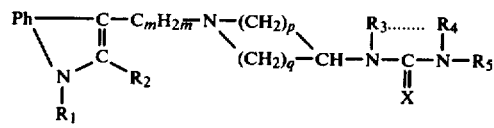

wherein Ph is unsubstituted 1,2-phenylene or 1,2-phenylene substituted by one member selected from lower alkyl, hydroxy, mercapto, lower alkoxy, lower alkenedioxy having 1 or 2 carbon atoms, benzyloxy, lower alkylmercapto, halogeno, triflouromethyl, nitro and amino; each of $R_1$ and $R_2$ is hydrogen or lower alkyl; $(R_3+R_4)$ is lower alkylene separating both nitrogens by 3 carbon atoms; $R_5$ is hydrogen, lower alkyl or phenyl unsubstituted or subsututed in the positions 3 to 6 as defined for Ph above; X is oxygen, sulfur, imino or lower alkylimino; m is an integer from 1 to 7; each of p and q is an integer from 1 to 3, but $(p+q)=4$; or a therapeutically acceptable acid addition salt thereof.

2. A compound as claimed in claim 1, in which formula Ph is 1,2-phenylene unsubstituted or monosubstituted by lower alkyl, hydroxy, mercapto, lower alkoxy, lower alkylenedioxy, benzyloxy, lower alkylmercapto, halogeno, trifluoromethyl, nitro or amino; each of $R_1$ and $R_2$ is hydrogen or lower alkyl; $(R_3+R_4)$ is lower alkylene separating both nitrogenes by 3 carbon atoms; $R_5$ is hydrogen, lower alkyl or phenyl unsubstituted or monosubstituted in the positions 3 to 6 as defined for Ph above; X is oxygen, sulfur, imino or lower alkylimino; m is an integer from 1 to 4; each of p and q is an integer from 1 to 3, but $(p+q)=4$; or a therapeutically acceptable acid addition salt thereof.

3. A compound as claimed in claim 1, in which formula Ph is 1,2-phenylene unsubstituted or substituted by hydroxy, mercapto or, alkyl, alkoxy or alkylmercapto each with up to 4 carbon atoms, benzyloxy, halogeno, trifluoromethyl, nitro or amino; each of $R_1$, $R_2$ and $R_5$ is hydrogen or alkyl with up to 4 carbon atoms $(R_3+R_4)$ is alkylene with 3 to 4 carbon atoms separating both nitrogens by 3 carbon atoms; X is oxygen, nitrogen or imino; m is an integer from 1 to 4 and each of p and q is the integer 2; or a therapeutically acceptable acid addition salt thereof.

4. A compound as claimed in claim 3 and corresponding to the formula

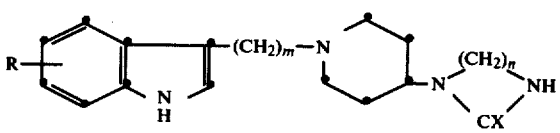

wherein R is hydrogen, hydroxy, mercapto or, alkyl, alkoxy or alkylmercapto each with up to 4 carbon atoms, benzyloxy, halogeno, trifluoromethyl, nitro or amino; m is an integer from 1 to 4; n is the integer 3 and X is oxygen, sulfur or imino; or therapeutically acceptable acid addition salts thereof.

5. A compound as claimed in claim 4, in which formula R is hydrogen, methyl, hydroxy, mercapto, methoxy, benzyloxy, methylmercapto, fluoro, chloro, bromo, trifluoromethyl, nitro or amino; m is an integer from 1 to 4; n is the integer 3 and X is oxygen, sulfur or imino; or a therapeutically acceptable acid addition salt thereof.

6. A compound as claimed in claim 4 and being the 1-(2-indolyl-3-ethyl)-4-(1,3-propyleneureido)-piperidine.

7. A hypotensive pharmaceutical composition comprising a pharmacologically effective amount of a compound claimed in claim 1, together with a pharmaceutical excipient.

8. A method for reducing the blood pressure in mammals, which comprises administering to them enterally or parenterally an effective amount of a composition claimed in claim 7.

* * * * *